United States Patent
Kiele et al.

(10) Patent No.: US 11,957,918 B2
(45) Date of Patent: Apr. 16, 2024

(54) IMPLANTABLE ELECTRICAL CONNECTOR ARRANGEMENT AND IMPLANTABLE ELECTRODE ARRANGEMENT

(71) Applicant: Albert-Ludwigs-Universität Freiburg, Freiburg (DE)

(72) Inventors: Patrick Kiele, Freiburg (DE); Cristian Pasluosta, Vorstetten (DE); Thomas Stieglitz, Freiburg (DE)

(73) Assignee: Albert-Ludwigs-Universität Freiburg, Freiburg (DE)

( * ) Notice: Subject to any disclaimer, the term of this patent is extended or adjusted under 35 U.S.C. 154(b) by 513 days.

(21) Appl. No.: 17/323,473

(22) Filed: May 18, 2021

(65) Prior Publication Data

US 2021/0268292 A1 Sep. 2, 2021

Related U.S. Application Data

(63) Continuation of application No. PCT/EP2019/081630, filed on Nov. 18, 2019.

(51) Int. Cl.
*A61N 1/375* (2006.01)
*A61N 1/05* (2006.01)
(Continued)

(52) U.S. Cl.
CPC ............ *A61N 1/3752* (2013.01); *A61N 1/05* (2013.01); *A61N 1/40* (2013.01); *H02J 50/05* (2016.02)

(58) Field of Classification Search
CPC .......... A61N 1/3752; A61N 1/05; A61N 1/40; H02J 50/05; H02J 2310/23
See application file for complete search history.

(56) References Cited

U.S. PATENT DOCUMENTS 9,493,261 B2   11/2016   Taff et al.
10,195,499 B2 *  2/2019   Stokke ............... A63B 53/0466
(Continued)

FOREIGN PATENT DOCUMENTS

DE   102014009136 A1   12/2015
DE   102015108467 A1   12/2016
EP      2110156 A2     10/2009

OTHER PUBLICATIONS

PCT International Search Report and Written Opinion, dated Jan. 23, 2020, 12 pages.

(Continued)

*Primary Examiner* — Briggitte R. Hammond
(74) *Attorney, Agent, or Firm* — Barley Snyder (57) ABSTRACT

An implantable electrical connector arrangement electrically connects a first electrical component and a second electrical component. The connector arrangement includes a first connector having a first terminal and a first coupling electrode connected to the first terminal and a second connector having a second terminal and a second coupling electrode connected to the second terminal. The first connector and the second connector are connectable to each other such that the first terminal and the second terminal are capacitively connectable via the first coupling electrode and the second coupling electrode in a connected state. A defined separation gap is formed between the first coupling electrode and the second coupling electrode in the connected state.

19 Claims, 7 Drawing Sheets

(51) Int. Cl.
*A61N 1/40* (2006.01)
*H02J 50/05* (2016.01)

(56) References Cited

U.S. PATENT DOCUMENTS

| | | |
|---|---|---|
| 2009/0237862 A1* | 9/2009 | Nielsen ................ A61N 1/378 29/25.03 |
| 2010/0099281 A1 | 4/2010 | Weiss et al. |
| 2015/0118898 A1 | 4/2015 | Paynter et al. |
| 2017/0365948 A1 | 12/2017 | Ehninger et al. |
| 2018/0050213 A1 | 2/2018 | Hauptmann |
| 2018/0221670 A1 | 8/2018 | Hauptmann |

OTHER PUBLICATIONS

E. Letechipia, P. H. Peckham, M. Gazdik, and B. Smith, "In-Line lead connector for use with implanted neuroprosthesis," "IEEE Trans. Biomed" Engl., vol. 38, No. 7, pp. 707-709, 1991.

M. Cocco, P. Dario, M. Toro, P. Pastacaldi, and R. Sacchetti, "An implantable neural connector incorporating microfabricated components," "J. Micromech. Microeng.", vol. 3, No. 4, pp. 219-221, 1993.

R. G. Hauser and B. J. Maron, "Lessons from the failure and recall of an implantable cardioverterdefibrillator," (Engl), "Circulation", vol. 112, No. 13, pp. 2040-2042, 2005.

"Craggs connector" from Finetech Medical, see P. E. Donaldson, "The Craggs connector: A termination for Cooper cable," (Engl), "Medical & biological engineering & computing", vol. 23, No. 2, pp. 195-196, 1985.

* cited by examiner

IMPLANTABLE ELECTRICAL CONNECTOR ARRANGEMENT AND IMPLANTABLE ELECTRODE ARRANGEMENT

CROSS-REFERENCE TO RELATED APPLICATIONS

This application is a continuation of PCT International Application No. PCT/EP2019/081630, filed on Nov. 18, 2019, which claims priority under 35 U.S.C. § 119 to German Patent Application No. 102018219831.4, filed on Nov. 20, 2018.

FIELD OF THE INVENTION

The present invention relates to an electrical connector arrangement and, more particularly, to an implantable electrical connector arrangement.

BACKGROUND

Implantable connectors play an important role in the manufacture and implantation of active implantable medical devices (AIMD). These typically consist of a housing that contains control electronics and a battery, implantable electrodes (or electrode arrays) and cables for establishing electrical contact with the electrodes and the electronics.

Reversibly detachable connectors (hereinafter also referred to as connectors), which are integrated into the cables, make it possible to separate the individual parts. This makes implantation easier and also creates the possibility of replacing defective, improved, or consumed parts (e.g. the battery in a pacemaker, which only has a lifespan of 3 to 7 years).

Such implants and connectors are shown e.g. in publications J. E. Letechipia, P. H. Peckham, M. Gazdik, and B. Smith, "In-Line lead connector for use with implanted neuroprosthesis," "IEEE Trans. Biomed" Engl., vol. 38, no. 7, pages 707-709, 1991; M. Cocco, P. Dario, M. Toro, P. Pastacaldi, and R. Sacchetti, "An implantable neural connector incorporating microfabricated components," "J. Micromech. Microeng.", vol. 3, no. 4, pages 219-221, 1993; as well as R. G. Hauser and B. J. Maron, "Lessons from the failure and recall of an implantable cardioverterdefibrillator," (Engl), "Circulation", vol. 112, no. 13, pages 2040-2042, 2005.

Depending on the desired number of channels and the desired integration density, the size of the connector increases, which in turn can have negative effects on the surrounding tissue. With conventional connector concepts, the insertion force is proportional to the number of contacts desired. In the case of miniaturized implantable connectors, the electrical insulation between the individual adjacent contacts of different channels is also a problem because a saturated, 100% moist environment prevails due to the use in the body. The electrical insulation must also be implemented and requires additional materials and forces. In order to ensure adequate electrical insulation, the distance between adjacent contacts in known connector arrangements must furthermore be comparatively large so that the integration density is not sufficiently high. The number of channels is therefore relatively limited and is at a maximum of 16 for known arrangements.

Once the two connector partners have been joined, adhesive must be applied in some known connector arrangements in order to create an insulation from the exterior. An example is the "Craggs connector" from Finetech Medical, see P. E. Donaldson, "The Craggs connector: A termination for Cooper cable," (Engl), "Medical & biological engineering & computing", vol. 23, no. 2, pages 195-196, 1985.

SUMMARY

An implantable electrical connector arrangement electrically connects a first electrical component and a second electrical component. The connector arrangement includes a first connector having a first terminal and a first coupling electrode connected to the first terminal and a second connector having a second terminal and a second coupling electrode connected to the second terminal. The first connector and the second connector are connectable to each other such that the first terminal and the second terminal are capacitively connectable via the first coupling electrode and the second coupling electrode in a connected state. A defined separation gap is formed between the first coupling electrode and the second coupling electrode in the connected state.

BRIEF DESCRIPTION OF THE DRAWINGS

The invention will now be described by way of example with reference to the accompanying Figures, of which.

DETAILED DESCRIPTION OF THE EMBODIMENT(S)

For better understanding of the present invention, it shall be explained in detail by way of embodiments with reference to the figures. Same elements are there designated with same reference numerals and same component designations. Furthermore, some features or combinations of features from the different embodiments shown and described can also be independent inventive solutions by themselves or solutions according to the invention.

Figure 1:
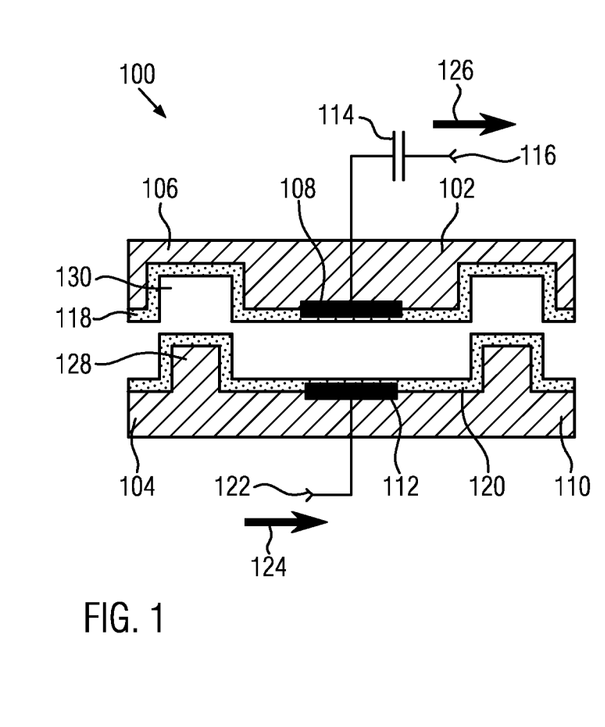
FIG. 1 is a schematic sectional view of a capacitive connector arrangement according to an embodiment prior to closing.

An implantable electrical connector arrangement 100 according to a first embodiment of the present invention shall first be explained in more detail below with reference to FIGS. 1 and 2. FIG. 1 shows a perspective view of the connector arrangement 100 in the not yet connected state. Connector arrangement 100 comprises a first connector 102 and a second connector 104. First connector 102 has a first substrate 106 on which at least one first coupling electrode 108 is arranged. Second connector 102 comprises a second substrate 110 with at least one second coupling electrode 112. First coupling electrode 108 is connected via a smoothing capacitor 114 or integrated capacitor 114 to a first terminal 116. Of course, smoothing capacitor 114 is only optional. First terminal 116 can be connected, for example, to a stimulation electrode. The concept according to the invention can be used for stimulating electrodes which provide an electrical driver.

The electrically insulating material of both substrates 106, 110 can be flexible or rigid depending on the configuration, but should not be electrically conductive. In the case of electrically conductive material, additional insulation layers must be introduced. For example, polyimide, PDMS, ceramic, and all other materials that are used for electrical circuit carriers are suitable.

Figure 2:
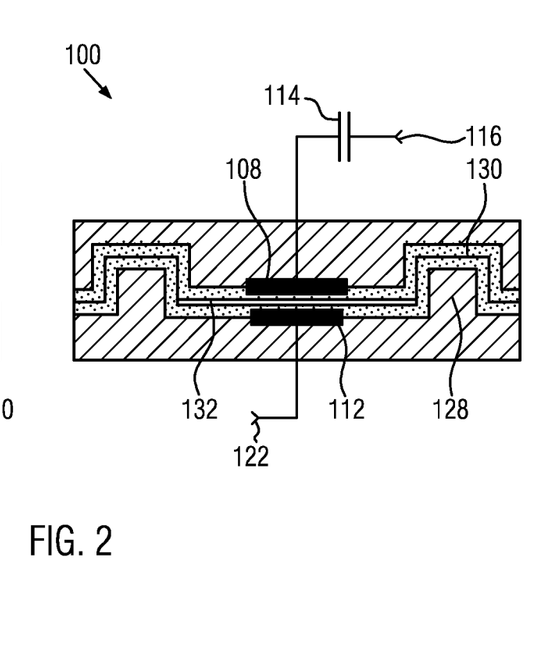
FIG. 2 is a schematic sectional view of the capacitive connector arrangement of FIG. 1 after the connection has been closed.

Second coupling electrode 112 is electrically connected to a second terminal 122, as shown in FIGS. 1 and 2. Second terminal 122 can be connected, for example, to driver electronics.

In the connected state shown in FIG. 2, first coupling electrode 108 and second coupling electrode 112 form the two plates of a capacitor. An input signal 124 can be fed in at first terminal 122, and an output signal 126 can correspondingly be output via two coupling electrodes 108, 112 and smoothing capacitor 114 at terminal 116. The connector arrangement 100 in the connected state is used to electrically connect a first electrical component, such as the stimulation electrode connected to the first terminal 116, to a second electrical component, such as the driver electronics connected to the second terminal 122.

Coupling electrodes 108, 112 can be formed by alloys such as platinum-iridium or MP35N®. MP35N® is a registered trademark of Standard Pressed Steel Technologies, Inc. The components of MP35N® ensure excellent corrosion resistance of the alloy, as all four alloy components, nickel, cobalt, chromium and molybdenum, increase corrosion resistance in almost all stainless steel, nickel, and cobalt alloys employed in the industry. The proportion of 20% chromium improves the resistance to oxidation, sulphidation, and chemical reactions with salt at elevated temperatures. Any other electrically conductive electrode material can of course also be used.

For electrical insulation and for protection against the external environment, an electrically insulating passivation layer 118, 120 is provided on first and second connector 102, 104, respectively, as shown in FIGS. 1 and 2. An adjustment protrusion 128 which, for example, surrounds the actual contact region around coupling electrode 112 in a circular or rectangular manner, is provided for interacting with an associated adjustment recess 130 in order to align first and second connector 102, 104 relative to one another. The adjustment protrusion 128 and the adjustment recess 130 may also be referred to as first and second adjustment structures or first and second alignment structures. The adjustment structures 128, 130, firstly, facilitate joining the two connectors 102, 104 together and, secondly, prevent the closed connection from slipping during operation.

FIG. 2 shows the capacitive connection according to the invention of the arrangement 100 in the plugged state. Adjustment protrusion 128 is received in adjustment recess 130 and first coupling electrode 108 is disposed across from second coupling electrode 112, so that a coupling capacitor is formed. According to the invention, the dimensions of adjustment recess 130 and adjustment protrusion 128 are selected such that, in the connected state, a defined separating gap 132 remains between first passivation layer 118 and second passivation layer 120 in the region of coupling electrodes 108, 112. The adjustment structures 128, 130 can also be used to adjust a width of the defined separation gap 132.

The present invention is based on the idea that capacitive coupling (displacement current) is used instead of galvanic faradic transmission (line current). Since the electrical coupling of the two connectors 102, 104 is capacitive, low frequencies are blocked. An additional smoothing capacitor can be integrated in order to nevertheless obtain low stimulation frequencies at the electrode in the case of use with a stimulation electrode. The actuation circuit outputs an excitation signal that has a higher frequency than a signal that is output to the implantable electrode.

According to the invention, the separating gap 132 can be filled with water or electrolyte during operation, so that an improved dielectric is created between two coupling electrodes 108, 112. In this case, separating gap 132 fills with liquid from the surrounding medium and/or with water which emerges from first and second passivation layers 118, 120 during operation.

In general, silicone rubber (polydimethylsiloxane, PDMS) is typically chosen as the insulator material, such as fort the passivation layers 118, 120, for use in implantable components. PDMS has the sufficient long-term stability that must be demanded for years of use in an aqueous or moist environment, as is present for an active implantable assembly. In the event that the separating gap 132 is at least in part defined by silicone material, it was possible to show that osmosis effects in the implanted state cause condensation water to escape from the silicone material and fill the separating gap 132. Such a layer of water with a high relative dielectric constant represents a good dielectric for the capacitive coupling. In addition, no measures have to be taken to prevent the ingress of liquid into the connector arrangement 100. This increases the long-term stability of the connection and thereby reduces the likelihood of failure.

Due to this type of connection, no contact pressure needs to be applied for establishing an electrical connection. The gap 132 with precisely defined dimensions is instead provided between the two contact 108, 112. According to an advantageous further development of the present invention, the separating gap 132 is not hermetically sealed off from the outside environment. When the connector arrangement 100 is implanted, water condenses in the separating gap 132. The significantly higher dielectric constant of water ($\sigma$, $H_2O=80$) compared to air ($\varepsilon r$, air=1) supports the capacitive coupling via the gap 132.

As indicated schematically in FIG. 2, first coupling electrode 108 has a slightly larger area than second coupling electrode 112 in order to compensate for any adjustment errors and to ensure reliable coupling.

In another embodiment, an implantable electrode arrangement according to the present invention comprises at least one implantable electrode and one implantable connector arrangement 100, where the at least one first terminal 116 is respectively connected to the at least one electrode and the at least one second terminal 122 is connectable to a control circuit.

Figure 3:
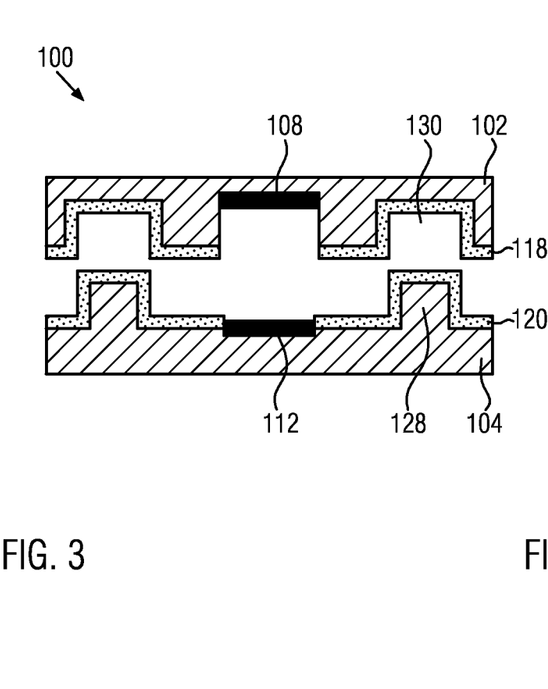
FIG. 3 is a schematic sectional view of a capacitive connector arrangement according to another embodiment prior to closing.

A further advantageous embodiment of connector arrangement 100 according to the invention shall be explained below with reference to FIGS. 3 and 4. Where the supply lines to terminals 116, 122, which in reality are disposed transverse to the plane of the drawing, and the terminals themselves are not shown. FIG. 3 shows the connector arrangement in the not connected state, while FIG. 4 shows the connector arrangement in the plugged state.

Figure 4:
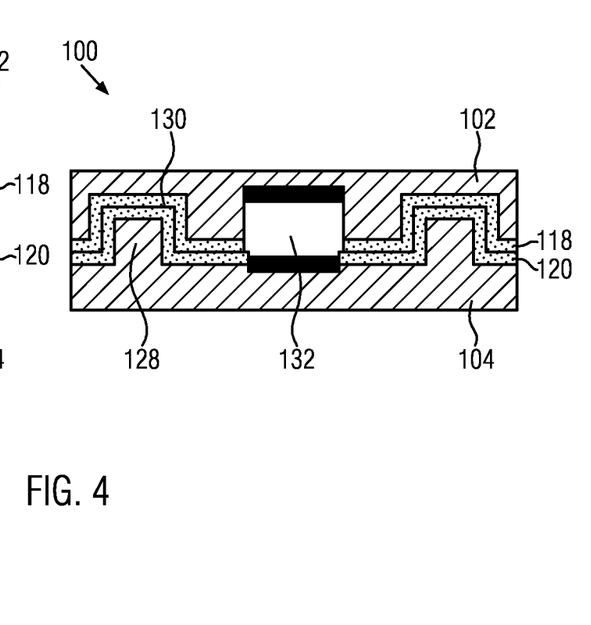
FIG. 4 is a schematic sectional view of the capacitive connector arrangement of FIG. 3 after the connection has been closed.

In the embodiment shown in FIGS. 3 and 4, first coupling electrode 108 and second coupling electrode 112 are not covered by a passivation layer. Furthermore, at least first coupling electrode 108 is stepped back into substrate 106 in order to create an even wider separating gap 132. Since there is no ohmic signal transmission, coupling electrodes 108, 112 do not necessarily have to be covered by an insulating layer as long as crosstalk to neighboring coupling electrodes is prevented. In this embodiment, first coupling electrode 108 has a slightly larger area than second coupling electrode 112 in order to compensate for any adjustment errors and to ensure reliable signal transmission.

Figure 5:
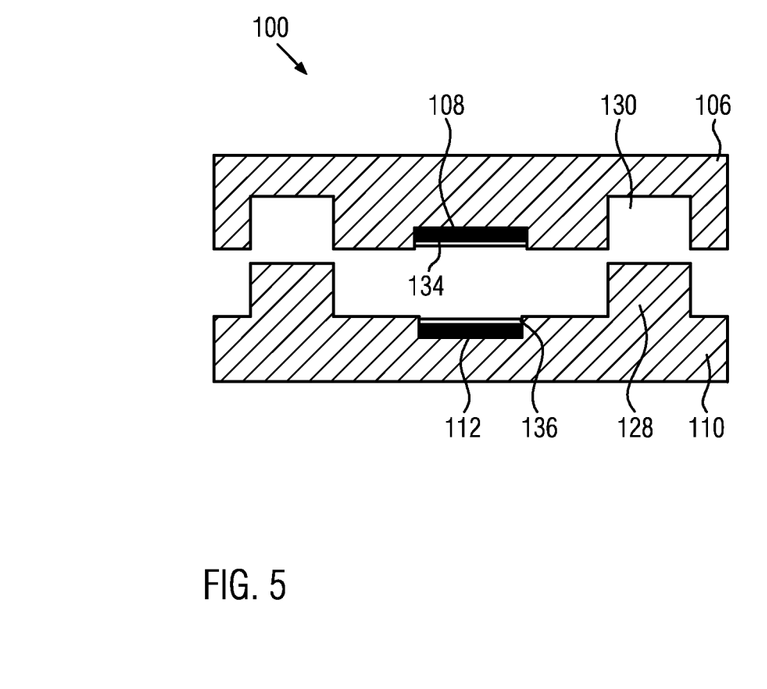
FIG. 5 is a schematic sectional view of a capacitive connector arrangement according to another embodiment prior to closing.
Figure 6:
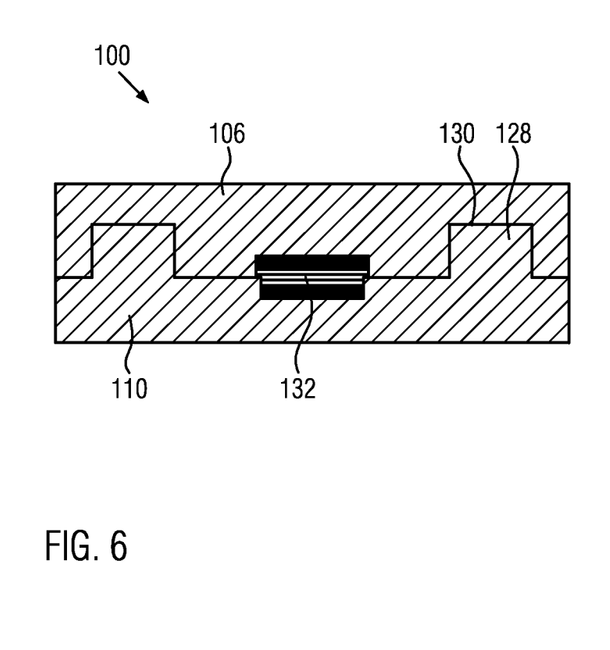
FIG. 6 is a schematic sectional view of the capacitive connector arrangement of FIG. 5 after the connection has been closed.

FIGS. 5 and 6 illustrate a further advantageous embodiment of a connector arrangement 100 according to the present invention. FIG. 5 shows connector arrangement 100 in the disconnected state, while FIG. 6 shows connector arrangement 100 in the connected state. In the embodiment shown in FIGS. 5 and 6, first and second coupling electrode 108, 112 are not covered over the entire surface by a passivation layer. Instead, a first local dielectric layer 134 is provided locally on the first coupling electrode 108 and a second local dielectric layer 136 is provided on second coupling electrode 112. The thicknesses of the two dielectric layers 134, 136 are selected such that, in interaction with adjustment protrusions 128 and adjustment recess 130, a defined gap 132 remains which fills with liquid during operation.

In contrast to ohmic contacts, the electrically conductive coupling electrodes 108, 112 do not need to be opened; i.e. the layer of insulating material 134, 136 can remain thereon. It can consist e.g. of polymers (Parylene-C, PDMS), oxides (TiOx) or other materials. Parylene-C, for example, is a material approved for human implantation and is electrically tight at a thickness of Various oxides achieve this electrical tightness already with significantly lower layer thicknesses and have a higher dielectric constant (e.g. εr, TiO2=63.7; εr, Paryiene-c=3.1). Both factors promise an increase in the coupling capacity and, accordingly, a better coupling. If no insulation is used, then the electrical coupling can be capacitive and resistive by way of accumulated water. In this case, however, adjacent contacts must be isolated from one another. The insulating material 134, 136 can but does not need to differ from the remainder of the encapsulation material of the connector (depending on the configuration, it is sufficient to provide different thicknesses for the insulating material and the encapsulation material for obtaining a directional capacitive coupling). In this way, the dielectric between the two coupling electrodes can be optimized for a particularly efficient capacitive coupling.

In the case of ohmic contacts, crosstalk between adjacent channels typically arises due to electrical leakage paths caused by the accumulation of water in voids that are present unintentionally. Such a resistive leakage path to adjacent channels is prevented due to the fact that a capacitive coupling is used in the concept according to the invention.

Figure 7:
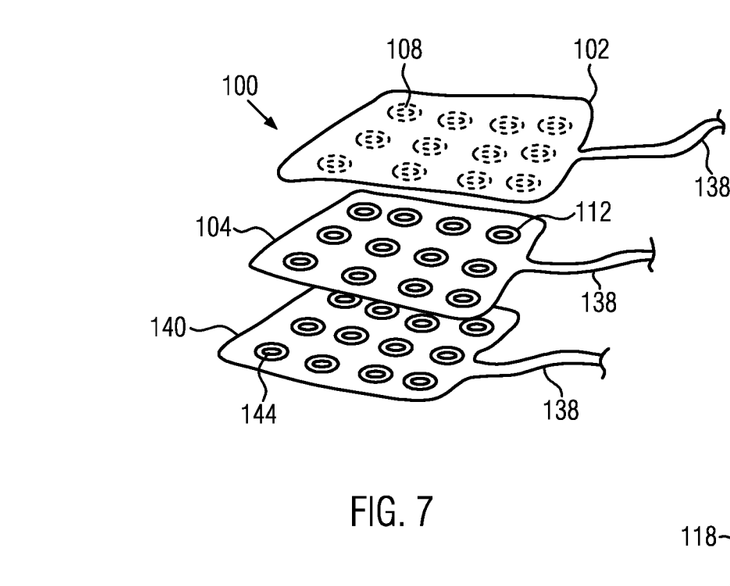
FIG. 7 is a schematic perspective view of a capacitive connector arrangement according to another embodiment prior to closing a connection.

FIG. 7 in a schematic perspective view shows an implantable connector arrangement 100 which comprises a plurality of capacitive contact arrangements according to the present invention. In particular, a first connector 102 and a second connector 104 are provided, each of which can be electrically connected to one another by way of an array of coupling electrodes 108, 112. Each of connectors 102, 104 comprises a line 138 which corresponds to the terminals 116, 122 shown in FIGS. 1 to 6. The substrates of first and second connectors 102, 104 are flexible in an embodiment in order to be able to mechanically adapt to their surroundings in the implanted state.

Figure 8:
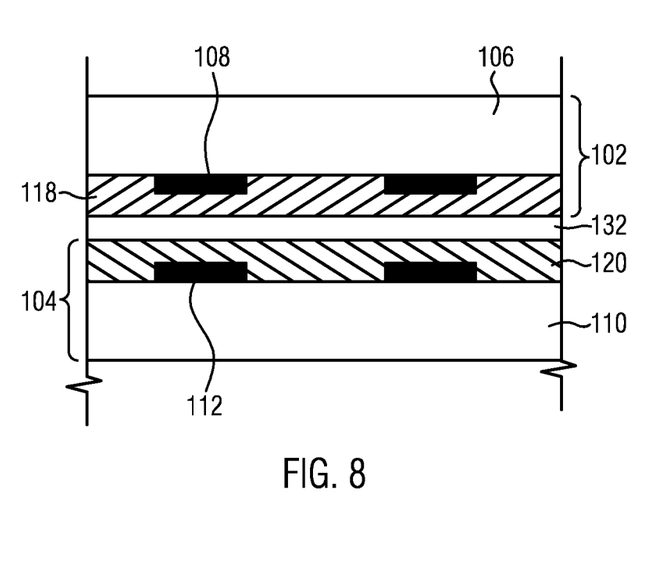
FIG. 8 is a schematic sectional view of a capacitive connector arrangement according to another embodiment after the connection has been closed.

According to a first embodiment, the capacitive connector arrangement comprises only first and second connector 102, 104. In this case, a schematic cross section looks as shown in FIG. 8. First connector 102 comprises a first substrate 106 that is, in an embodiment, produced from flexible electrically insulating material. Arranged on substrate 106 is an array of first coupling electrodes 108, each of which is connected to electrical supply lines that lead to electrical lines 138. Electrodes 108 can be configured in accordance with any of the embodiments of FIGS. 1 to 6.

As shown in FIG. 8, in an embodiment, a first passivation layer 118 is provided which covers coupling electrodes 108 in a planar manner. Second connector 104 also has a flexible electrically insulating substrate 110 and second coupling electrodes 112 that are arranged in an array that corresponds to the array of first coupling electrodes 108. A second passivation layer 120 covers coupling electrodes 112 in a planar manner. Respective spacers ensure that a separating gap 132 remains between first connector 102 and second connector 104.

In another embodiment, the second connector 104 also comprises coupling electrodes on its rear side. As shown in FIG. 7, a third connector 140 can then be connected to coupling electrodes on the rear side. This arrangement is shown as a schematic sectional view in FIG. 9. According to this embodiment, second connector 104 has capacitive coupling electrodes 150 both on a first side 146 of substrate 110 as well as on a second side 148 of substrate 110. Third connector 140 is constructed analogously to first connector 102 and comprises a third substrate 152 with third capacitive coupling electrodes 144. According to the invention, a separating gap 132 is also provided between coupling electrodes 150 on the rear side and third coupling electrodes 144.

Figure 9:
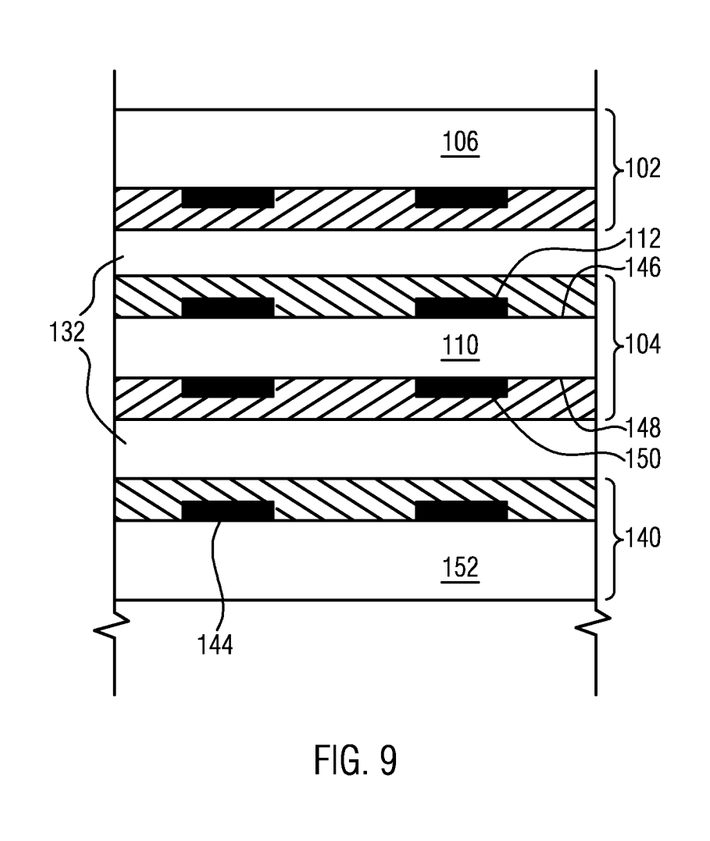
FIG. 9 is a schematic sectional view of the capacitive connector arrangement of FIG. 7 after the connection has been closed.

The multilayer arrangement shown in FIGS. 7 and 9 has the advantage that an even higher integration density can be obtained because adjacent electrodes are not connected by resistive leakage current paths. At the same time, the area used is reduced.

In addition to the simple planar arrangements that were explained with reference to FIGS. 1 to 9, the principles according to the invention can also be applied advantageously for various three-dimensional geometries.

Figure 10:
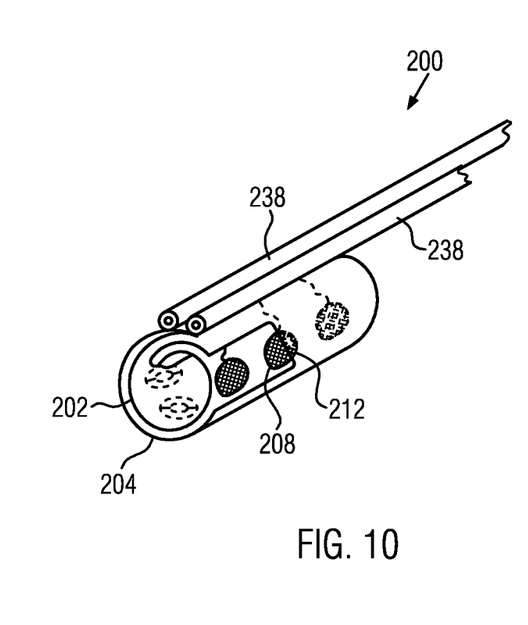
FIG. 10 is a schematic perspective view of a capacitive connector arrangement according to another embodiment.

FIG. 10 shows a capacitive connector arrangement 200 in which first connector 202 and second connector 204 are curled up to assume a substantially cylindrical three-dimensional shape. Coupling electrodes 208, 212 are arranged superimposed on one another once the two cylinders are pushed into one another to form a complete capacitor. This arrangement 200 is particularly space-saving and can be implemented particularly well with a capacitive connector arrangement because both connectors 202, 204 have a completely smooth surface. This arrangement 200 can be created, for example, in that the arrays of coupling electrodes are produced having a mechanical pretension so that they curl up with a defined radius. The radii are chosen such that the outer array applies an inwardly force and the inner array counteracts this force. A defined pressure is thereby applied to all contacts. Of course, with this arrangement as well, a separating gap is set between the coupling electrodes by way of appropriate adjustment devices or by way of structuring the contacts accordingly, as shown, for example, in FIG. 6. Supply lines 238 allow external components to be connected.

Figures 11, 12:
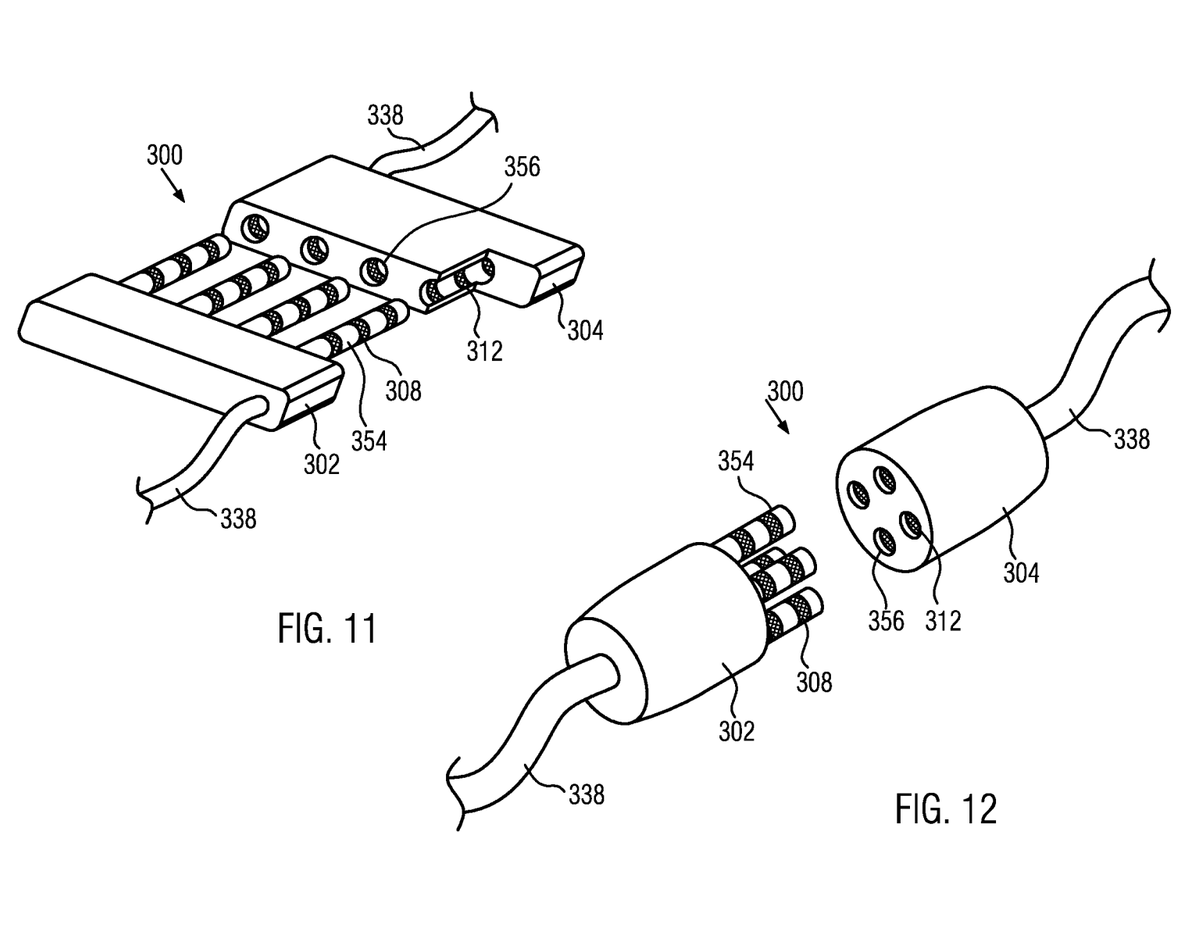
FIG. 11 is a schematic perspective view of a capacitive connector arrangement according to another embodiment.
FIG. 12 is a schematic perspective view of a capacitive connector arrangement according to another embodiment.

According to a further advantageous embodiment of implantable connector arrangement 300, shown in FIG. 11, first coupling electrodes 308 can also have an annular shape and be arranged on pin-shaped protrusions 354. Accordingly, annular second coupling electrodes 312 are then likewise arranged in the interior of socket-shaped recesses 356. Coupling electrodes 308, 312 are capacitively connected to one another by plugging two connectors 302, 304 together. Supply lines 338 allow for the connection of respective components to be contacted. Due to the specific geometric configuration of pin-shaped protrusions 354 and recesses 356, the pin-shaped protrusions 354 are arranged in the recesses 356 and a defined gap is set in the radial direction between annular coupling electrodes 308 and 312.

The spatial geometries of connectors 302, 304 can also be designed completely differently in other embodiments. Another example of such a three-dimensional connector-like structure is illustrated in FIG. 12. The advantage of such an arrangement can be seen in the fact that the connection is mechanically comparatively stable. Due to the provision of the separating gap and the capacitive coupling, no particularly high insertion forces are required and a seal against the moist environment is not necessary in the implanted state.

Figure 13:
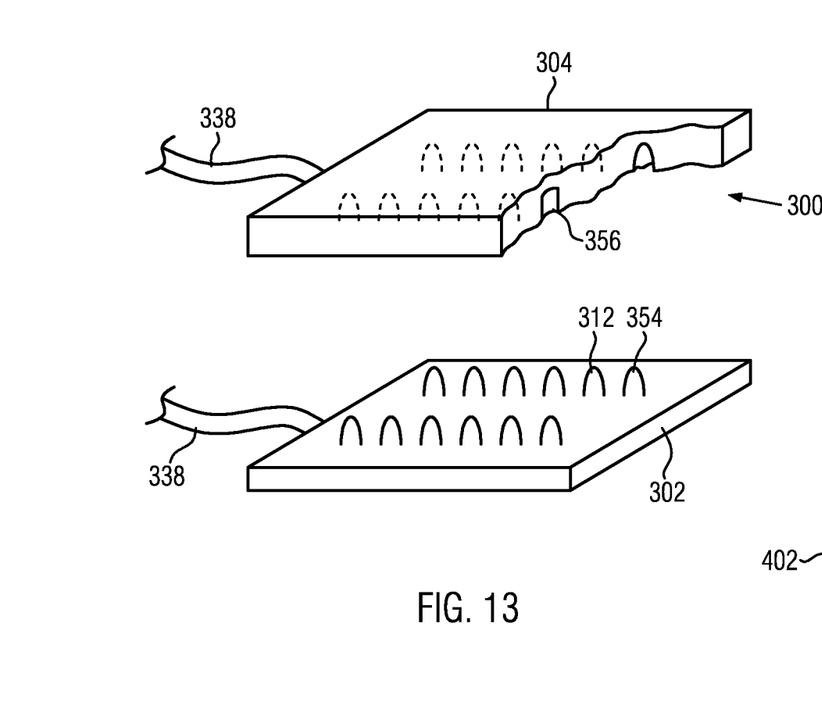
FIG. 13 is a schematic perspective view of a capacitive connector arrangement according to another embodiment.

A further variant of connector arrangement 300 with pins and sockets is shown in FIG. 13. In this embodiment, each protrusion 354 is provided with only one capacitive coupling electrode.

Figure 14:
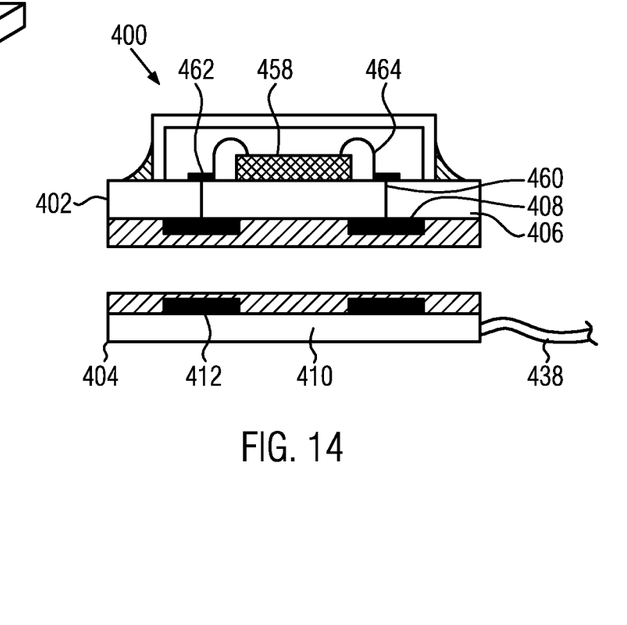
FIG. 14 is a schematic sectional view of a capacitive connector arrangement according to another embodiment.

FIG. 14 shows a further embodiment of a connector arrangement 400. Further electrical or electronic components can be integrated in one or both of connectors 402, 404; these can be electronic actuation and evaluation circuits, but also passive components such as additional resistors, capacitors, and coils. FIG. 14 shows by way of example the integration of an electronic component 458 into a connector arrangement 400. In connector arrangement 400 shown, first connector 402 is provided with an electronic component 458 on the side of substrate 406 facing away from coupling electrodes 408. Coupling electrodes 408 are connected to bond pads 462 by way of metallized vias 460. Electronic component 458 can be connected to bond pads 462 by way of bond wires 464. A housing 466 or a potting compound can encapsulate electronic component 458. In other embodiments, surface mount device (SMD) components (or any other suitable assembly and connection technology) can also be used. Second connector 404 is formed by a respective planar array of capacitive coupling electrodes 412 on a substrate 410. An electrical line 438 allows external components to be connected.

In summary, the present invention provides a capacitive, implantable, reversible, and multi-channel connection. Condensed or ingressing water at the point of coupling is used as a desired effect for capacitive coupling of two connectors. This arrangement advantageously provides the scalability of the number of electrical channels at a constant insertion force. A multi-channel, reversible, and implantable connection can thus be realized without the need for electrical insulation structures between two or more channels. The ingress of water cannot cause short circuits and therefore does not have to be prevented. The connector according to the embodiments of the invention is reusable, whereby the part connected to the implanted electrode can remain in situ when the components connected to the other part need to be repaired.

The implantable connector arrangement according to the present invention allows even densely packed contact arrays to be connected reliably as well as with long-term electrical and mechanical stability. The connector arrangement is inexpensive and, moreover, is biocompatible and certifiable for chronic use.

What is claimed is:

1. An implantable electrical connector arrangement for electrically connecting a first electrical component and a second electrical component, the connector arrangement comprising:
a first connector having a first terminal and a first coupling electrode connected to the first terminal; and
a second connector having a second terminal and a second coupling electrode connected to the second terminal, the first connector and the second connector are connectable to each other such that the first terminal and the second terminal are capacitively connectable via the first coupling electrode and the second coupling electrode in a connected state, a defined separation gap is formed between the first coupling electrode and the second coupling electrode in the connected state.

2. The implantable electrical connector arrangement of claim 1, wherein the defined separation gap is not hermetically sealed against an outside environment.

3. The implantable electrical connector arrangement of claim 1, wherein the defined separation gap is defined at least in part by a silicone material.

4. The implantable electrical connector arrangement of claim 1, wherein the first coupling electrode and the second coupling electrode are each coated with an electrically insulating material.

5. The implantable electrical connector arrangement of claim 1, wherein the first connector has a first adjustment structure and the second connector has a second adjustment structure, the first adjustment structure and the second adjustment structure interact in the connected state to adjust a width of the defined separation gap.

6. The implantable electrical connector arrangement of claim 1, wherein the first connector and/or the second connector has an integrated capacitor.

7. The implantable electrical connector arrangement of claim 1, wherein the first connector and/or the second connector has an electrically insulating substrate.

8. The implantable electrical connector arrangement of claim 1, wherein the first connector has an array of first coupling electrodes connected in the connected state to an array of second coupling electrodes of the second connector.

9. The implantable electrical connector arrangement of claim 1, further comprising a third connector having a third terminal and a third coupling electrode connected to the third terminal.

10. The implantable electrical connector arrangement of claim 9, wherein the second connector has a fourth terminal and a fourth coupling electrode connected to the fourth terminal.

11. The implantable electrical connector arrangement of claim 10, wherein the third coupling electrode and the fourth coupling electrode are capacitively coupled in the connected state and a second separating gap is formed between the third coupling electrode and the fourth coupling electrode.

12. The implantable electrical connector arrangement of claim 11, wherein the first connector, the second connector, and the third connector each have a substrate with a plurality of coupling electrodes arranged thereon.

13. The implantable electrical connector arrangement of claim 10, wherein the second connector has the second coupling electrode on a first side of a substrate and the fourth coupling electrode on a second side of the substrate opposite the first side.

14. The implantable electrical connector arrangement of claim 1, wherein the first connector and the second connector are curled up and have a cylindrical three-dimensional shape.

15. The implantable electrical connector arrangement of claim 1, wherein the first connector has a pin-shaped protrusion on which the first coupling electrode is arranged.

16. The implantable electrical connector arrangement of claim 15, wherein the second connector has a recess receiving the pin-shaped protrusion at least in part, the second coupling electrode is arranged in the recess.

17. The implantable electrical connector arrangement of claim 1, wherein at least one of the first connector and the second connector has an integrated electronic component.

18. An implantable electrode arrangement, comprising:
an implantable electrode; and
an implantable electrical connector arrangement including a first connector having a first terminal and a first coupling electrode connected to the first terminal and a second connector having a second terminal and a second coupling electrode connected to the second terminal, the first connector and the second connector are connectable to each other such that the first terminal and the second terminal are capacitively connectable via the first coupling electrode and the second coupling electrode in a connected state, a defined separation gap is formed between the first coupling electrode and the second coupling electrode in the connected state, the first terminal is connected to the implantable electrode and the second terminal is connectable to an actuation circuit.

19. The implantable electrode arrangement of claim 18, further comprising a smoothing capacitor arranged between the implantable electrode and the first coupling electrode.

* * * * *